(12) United States Patent
Oreper et al.

(10) Patent No.: US 7,660,391 B2
(45) Date of Patent: Feb. 9, 2010

(54) COMPACT E-BEAM SOURCE FOR GENERATING X-RAYS

(75) Inventors: Boris Oreper, Newton, MA (US); Richard Franklin Eilbert, Lincoln, MA (US)

(73) Assignee: L-3 Communications Security and Detection Systems Inc., Woburn, MA (US)

(*) Notice: Subject to any disclaimer, the term of this patent is extended or adjusted under 35 U.S.C. 154(b) by 73 days.

(21) Appl. No.: 11/903,035

(22) Filed: Sep. 20, 2007

(65) Prior Publication Data

US 2008/0075230 A1 Mar. 27, 2008

Related U.S. Application Data

(60) Provisional application No. 60/846,164, filed on Sep. 21, 2006.

(51) Int. Cl.
*H01J 35/08* (2006.01)
*H01J 35/14* (2006.01)
(52) U.S. Cl. .................... 378/123; 378/138
(58) Field of Classification Search .......... 378/119, 378/121, 123, 136–139
See application file for complete search history.

(56) References Cited

U.S. PATENT DOCUMENTS

| 5,490,193 | A | 2/1996 | Kuroda et al. |
| 6,628,745 | B1 | 9/2003 | Annis et al. |
| 7,233,644 | B1 | 6/2007 | Bendahan et al. |

FOREIGN PATENT DOCUMENTS

| EP | 0 455 177 A2 | 11/1991 |
| EP | 0 455 177 A3 | 11/1991 |
| WO | WO 92/03837 A1 | 3/1992 |

OTHER PUBLICATIONS

International Search Report and Written Opinion for International Application No. PCT/US2007/020542 dated Jul. 17, 2008.

*Primary Examiner*—Irakli Kiknadze
(74) *Attorney, Agent, or Firm*—Wolf, Greenfield & Sacks, P.C.

(57) ABSTRACT

Various novel apparatuses and methods for generating X-rays are disclosed. In some embodiments, for example, an apparatus may be configured and arranged so that, for at least one interception point on a particular portion of a scan path on a surface of a target along which a steering element steers an accelerated electron beam (e-beam), both an angle and its complement between a line corresponding to a direction in which the accelerated e-beam is traveling at the interception point and a line oriented normal to the surface of the target at such interception point are greater than forty five degrees.

26 Claims, 7 Drawing Sheets

COMPACT E-BEAM SOURCE FOR GENERATING X-RAYS

RELATED APPLICATIONS

This application claims the benefit under 35 U.S.C. §119 (e) of U.S. Provisional Application Ser. No. 60/846,164, entitled COMPACT E-BEAM SOURCE FOR GENERATING X-RAYS, filed Sep. 21, 2006. This disclosure also relates at least in part to the subject matter described in co-owned U.S. Application Ser. No. 60/696,669 and U.S. Patent Publication No. US2007/0081623 A1, both entitled METHODS AND APPARATUS FOR E-BEAM SCANNING. The entire contents of each of the foregoing documents is incorporated herein by reference.

FIELD

The inventions disclosed herein relate generally to scanning systems that generate X-rays by directing one or more electron beams (e-beams) at a target.

BACKGROUND

X-ray imaging technology has been employed in a wide range of applications from medical imaging to detection of unauthorized objects or materials in baggage, cargo or other containers generally opaque to the human eye. X-ray imaging typically includes passing high energy radiation (i.e., X-rays) through an object to be imaged. X-rays from a source passing through the object interact with the internal structures of the object and are altered according to various characteristics of the material (e.g., transmission, scattering and diffraction characteristics, etc.) that the X-rays encounter. By measuring changes (e.g., attenuation, energy spectrum, scatter angle, etc.) in the X-ray radiation that exits the object, information related to characteristics of the material such as density, atomic structure and/or atomic number, etc., may be obtained.

Many X-ray scanning systems employ electron beam (e-beam) technology to generate X-rays that penetrate an object of interest to investigate the object's properties. In e-beam technology, an e-beam is directed to impinge on the surface of a target responsive to the e-beam. The target may be formed from, for example, tungsten, molybdenum, gold, or other material that emits X-rays in response to an e-beam impinging on its surface. For example, the target may be a material that converts energy in the e-beam into relatively high energy photons, emitted from the target essentially in the $4\pi$ directions. The released energy may be shaped or collimated by blocking selected portions of the X-rays emitted from the target using any of various radiation absorbing material (such as lead). For example, the X-ray may be collimated to form a cone beam, a fan beam, a pencil beam or any other X-ray beam having generally desired characteristics. The collimated X-rays may then pass into an inspection region to penetrate an object of interest to ascertain one or more characteristics of the object.

An e-beam may be generated, for example, from an electron source, the electrons being accelerated and directed as desired along the surface of the target. For example, a generated e-beam may be directed magnetically by bending the beam using one or more magnetic coils, herein referred to as steering coils. In general, the e-beam propagates in a vacuum chamber until the e-beam impinges on the target. Various methods (e.g., bending an e-beam using one or more magnets) of steering an e-beam along a desired path over a surface of the target are well known in the art.

To measure X-ray radiation penetrating an object to be imaged, an array of detectors responsive to X-ray radiation typically is arranged about the object being imaged. Each detector in the array responds to X-rays impinging on its surface to provide a radiograph or view indicative of the total absorption (i.e., attenuation) incurred by material substantially in a line between the X-ray source and a detector in the array. The term "X-ray source" refers generally to an origin or origins of X-ray radiation. In e-beam technology, the X-ray source is typically the locations or points at which the e-beam impinges on the target, thus emitting X-rays from those locations in response to the e-beam. The X-ray source and detector array may be moved relative to one another to obtain a number of views of the object at different angles.

Conventional X-ray systems that are used for computed tomography (CT) scanning establish a circular relationship between an X-ray source and its corresponding detector array. For example, an X-ray source and corresponding detector array may both be rotated together along a circular path. Alternatively, a stationary circular array of detectors may be provided and a source may be rotated about a portion of a circular path (e.g., by providing an e-beam along a circular scanning path on a target). X-ray systems having a circular geometry typically arrange detectors (or detector locations) equidistant from a common point. To generate X-rays that penetrate an inspection region over a number of different viewing angles (e.g., over 180°), a circular target arranged substantially concentric with and diametrically opposed to the detectors is often employed. An e-beam is then typically directed generally in a line through the center point and then deflected such that the e-beam impinges on the target along a circular path. The resulting X-rays then penetrate the object of interest at a desired number of angles or views.

SUMMARY

According to one aspect of the present invention, an apparatus for generating X-rays comprise a vacuum chamber, a target, an electron accelerator, and a steering element. The apparatus is configured and arranged so that one or more of the following criteria are met: (A) for at least one interception point on a particular portion of a scan path on the surface of the target along which the steering element steers an accelerated electron beam (e-beam), both an angle and its complement between a line corresponding to a direction in which the accelerated e-beam is traveling at the interception point and a line oriented normal to the surface of the target at such interception point are greater than forty five degrees; (B) for at least one interception point on the particular portion of the scan path on the surface of the target along which the steering element steers the accelerated e-beam, either an angle or its complement between a line corresponding to a direction in which the accelerated e-beam is traveling at the interception point and a line that is tangent to the scan path at such interception point is less than forty five degrees; (C) for at least one interception point on the particular portion of the scan path on the surface of the target along which the steering element steers the accelerated e-beam, both an angle and its complement between a line corresponding to a direction in which the accelerated e-beam is traveling at the e-beam origination point of the steering element and a line oriented normal to a surface of the target at such interception point are greater than forty five degrees; (D) for at least one interception point on the particular portion of the scan path on the surface of the target along which the steering element steers the accelerated e-beam, either an angle or its complement between a line corresponding to a direction in which the accelerated e-beam is traveling at an e-beam origination point of the steering element and a line that is tangent to the scan path at such interception point is less than forty five degrees; (E) a minimal distance between the e-beam origination point of the steering element and the particular portion of the scan path on the surface of the target along which the steering element steers the accelerated e-beam is less than fifty percent of a maximal distance between the e-beam origination point of the steering element and the particular portion of the scan path on the surface of the target along which the steering element steers the accelerated e-beam; (F) for each interception point on the particular portion of the scan path on the surface of the target along which the steering element steers the accelerated e-beam, a maximum dimension of the interior cavity of the vacuum chamber, measured in a plane that contains such interception point and to which a line that is tangent to the scan path at such interception point is normal, is less than fifty percent of a total e-beam scan distance along the particular portion of the scan path on the surface of the target along which the steering element steers the accelerated e-beam; and (G) for each interception point on the scan path on the surface of the target, a maximum dimension of the interior cavity of the vacuum chamber, measured in a plane that contains such interception point and to which a line that is tangent to the scan path at such interception point is normal, is less than fifty percent of a total e-beam scan distance along the scan path on the surface of the target.

According to another aspect, an apparatus for generating X-rays comprises a vacuum chamber, a target, an electron accelerator, and first and second steering elements. The first steering element is configured and arranged to steer the accelerated e-beam through an interior cavity of the vacuum chamber and a substantial distance along a first portion of a surface of the target so as to cause X-rays to emanate from the target and into an inspection region located outside the interior cavity of the vacuum chamber. The second steering element is configured and arranged to steer the accelerated e-beam through the interior cavity of the vacuum chamber and a substantial distance along a second portion of the surface of the target, which is at least partially non-overlapping with the first portion of the surface of the target, so as to cause X-rays to emanate from the target and into the inspection region.

According to another aspect, a method for generating X-rays involves the use of first and second steering elements to steer an accelerated e-beam. The first steering element steers the accelerated e-beam a substantial distance along a first portion of a surface of a target so as to cause X-rays capable of penetrating objects of interest for inspection purposes to emanate from the target and into an inspection region. The second steering element steers the accelerated e-beam a substantial distance along a second portion of the surface of the target, which is at least partially non-overlapping with the first portion of the surface of the target, so as to cause X-rays capable of penetrating objects of interest for inspection purposes to emanate from the target and into the inspection region.

The generated X-rays may, for example, be collimated into a moving beam that passes through a tunnel of a CT scanner.

DETAILED DESCRIPTION

Figure 1:
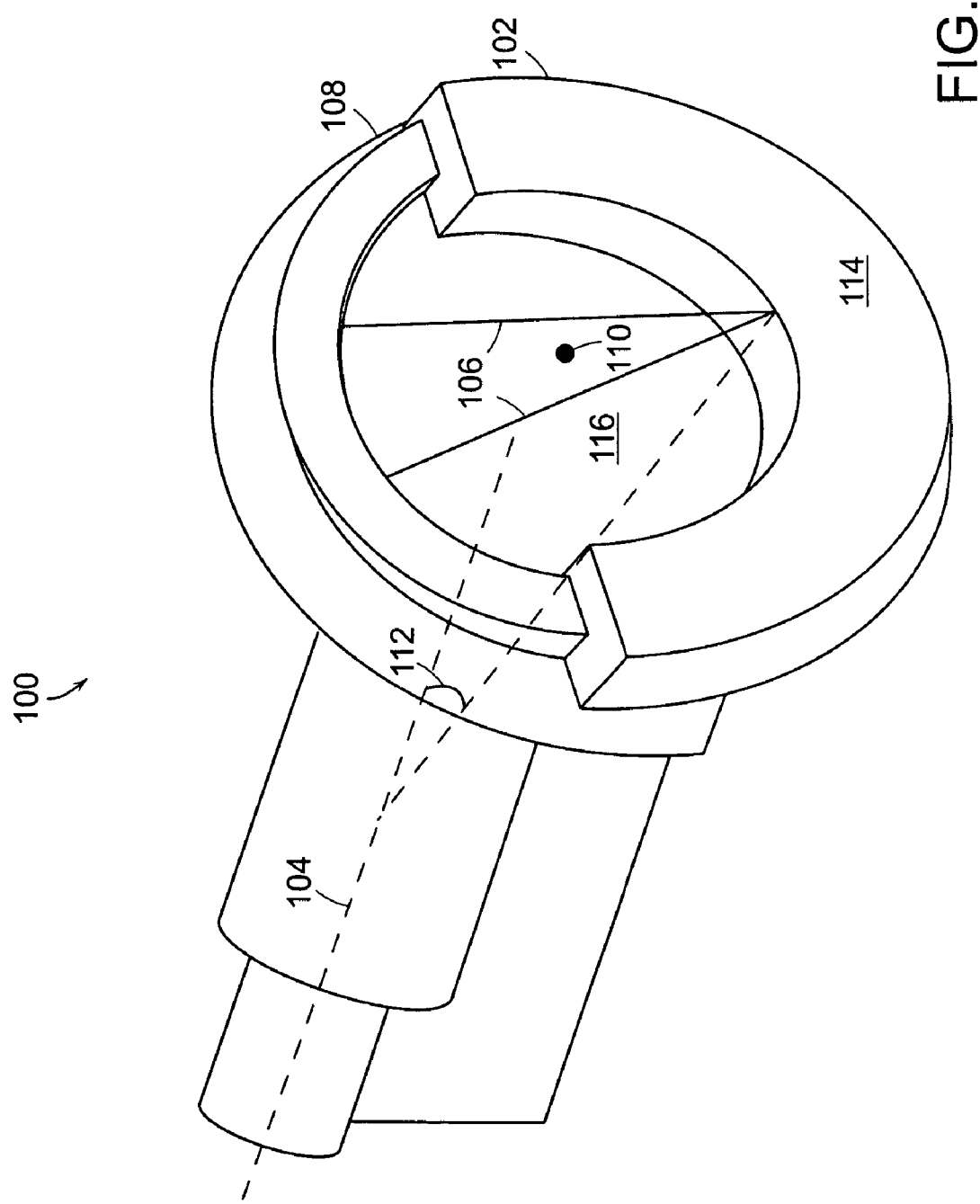
FIG. 1 shows a conventional circular geometry x-ray scanning system using e-beam technology.

We have recognized that the size, cost, and complexity of electron beam (e-beam) scanning apparatuses can be reduced significantly by orienting one or more e-beam generators at non-conventional locations with respect to the target of the device. As discussed above, conventional X-ray scanning systems employ a circular geometry between a detector array and a corresponding X-ray source. FIG. 1 illustrates schematically an X-ray scanning system 100 employing e-beam technology in a circular geometry. The X-ray scanning system 100 includes a circular target 102 that responds to an impinging e-beam 104 by emitting X-rays 106 and a circular array of detectors 108 responsive to the radiation.

The e-beam 104 is directed essentially along a longitudinal axis that penetrates a center point 110 of the detector array (or target). One or more magnetic coils (not shown in FIG. 1) deflect the e-beam from the longitudinal axis at a deflection angle 112 so that the e-beam impinges on the target 102, for example, at location 114 on the target 102. The resulting X-rays 106 then penetrate an inspection region 116 and impinge on the detector array 108. As the e-beam 104 is directed along a circular arc of the target 102, the resulting X-rays 106 penetrate the inspection region 116 at different angles to provide different projections or views of an object (not shown) positioned within the inspection region 116.

Other circular geometry systems and methods related to e-beam scanning are described in U.S. Pat. No. 5,491,734 ('734) to Boyd et al., U.S. Pat. No. 4,352,021 ('021) to Boyd et al., and U.S. Pat. No. 6,735,271 ('271) to Rand et al., all of which are incorporated herein by reference in their entirety.

Various technical constraints limit the amount the e-beam can be practicably deflected. That is, design specifications may be deflection angle limited. Accordingly, the distance between an e-beam source and the target is often extended so that deflection angle constraints can be met, while still accommodating a particular detector array circumference. For example, the distance between e-beam source and the center point 110 may be increased so that a smaller deflection angle 112 is sufficient to allow the e-beam to impinge on the target 102. However, the vacuum chamber and the corresponding components needed to enclose the path of the e-beam are relatively expensive and bulky. In addition, the extended vacuum region has relatively long field-free paths between the e-beam source point and the target, which require more extensive shielding and may be susceptible to stray electromagnetic (EM) fields. As a result, such systems are more costly to manufacture and more cumbersome to deploy due to the increased footprint, shielding requirements, etc.

We have appreciated that arbitrary geometries may offer a number of benefits with respect to the flexibility of the design and may facilitate more compact and inexpensive X-ray detection systems. We have identified and developed various e-beam techniques for use in arbitrary geometry systems that facilitate relatively inexpensive, compact and efficient X-ray detections systems.

Figure 2:
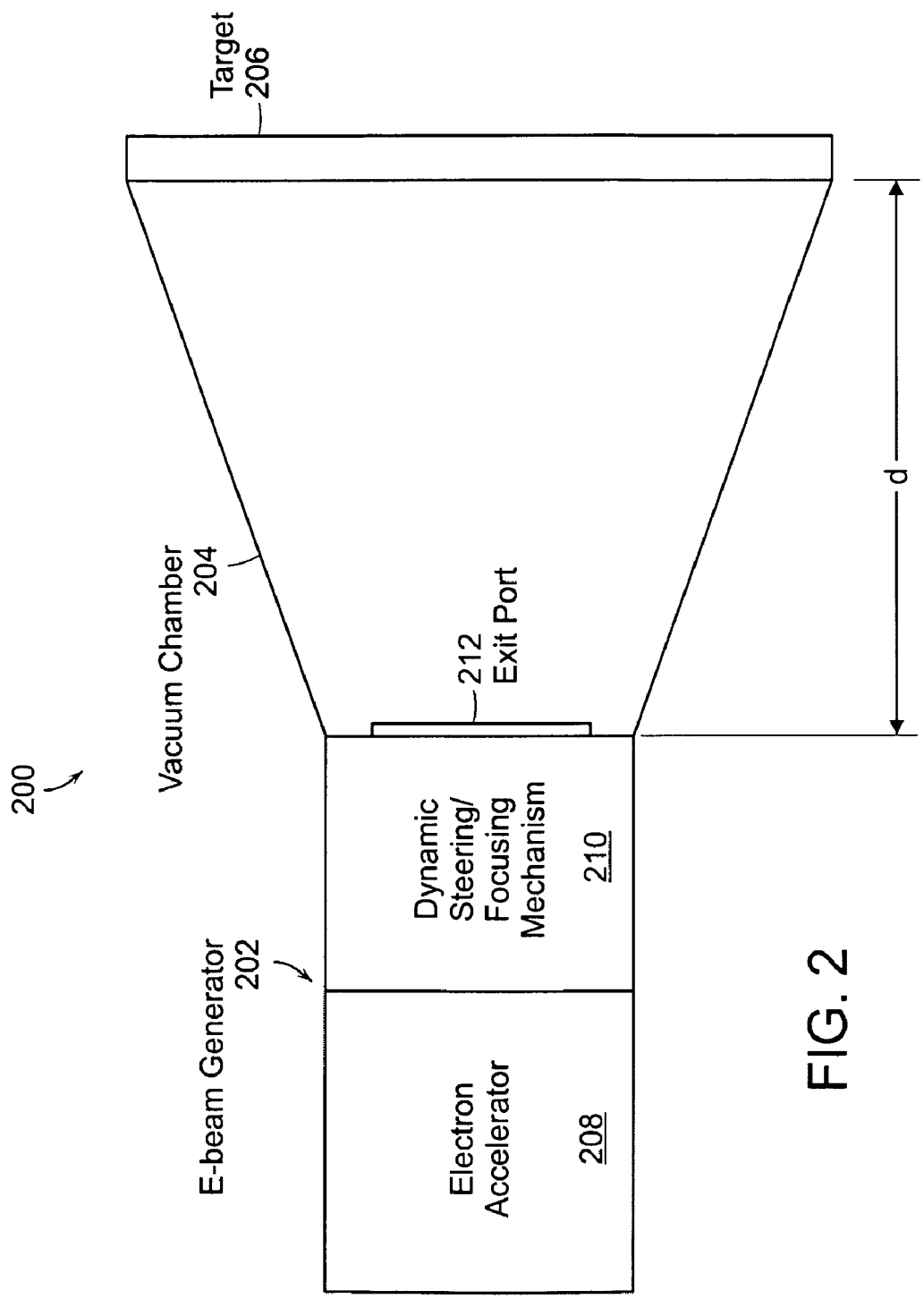
FIG. 2 shows a conceptual view of an apparatus for generating X-rays comprising components that can be used in various embodiments of the invention.

FIG. 2 illustrates conceptually the various components of an apparatus 200 that may be used to generate X-rays in accordance with various aspects of the present invention. The same or similar components as those described may be employed in various embodiments of the invention, including the particular illustrative embodiments described below in connection with FIGS. 3-7. As shown, the apparatus 200 includes an e-beam generator 202 that may be adapted to sweep an e-beam (not shown in FIG. 2) within a vacuum chamber 204 along a linear or curvilinear scan path on a target 206 to generate X-rays used to inspect objects of interest. The e-beam generator 202 in the illustrated example includes an electron accelerator 208 adapted to accelerate electrons to an appropriate velocity to create an e-beam suitable for generating X-rays of a desired energy. Various electron/particle accelerators are well known in the art. In some embodiments, the electron accelerator 208 may be capable of accelerating the e-beam to an energy of at least 40 KeV so as to allow the generation of X-rays having an energy sufficient to penetrate objects of interest for inspection purposes. In certain embodiments intended to allow inspection of thicker or more dense objects, the electron accelerator 208 may be capable of accelerating the e-beam to an energy greater than 50 KeV, or greater than 60 KeV, or greater than 70 KeV, or greater than 80 KeV, or greater than 90 KeV, or greater than 100 KeV, or greater than 110 KeV, or greater than 120 KeV, or greater than 130 KeV, or greater than 140 KeV, or greater than 150 KeV, or greater than 160 KeV, or greater than 170 KeV, or greater than 180 KeV, or greater than 190 KeV, or perhaps even greater than 200 KeV. For at least certain medical imaging applications, an e-beam energy of about 40 KeV may be suitable. For baggage inspection or similar security inspection applications, an electron beam energy of about 160 KeV may be suitable in at least some circumstances.

After the electrons have been suitably accelerated, the resulting e-beam may enter a dynamic steering/focusing mechanism 210, referred to hereinafter as the steering mechanism. The steering mechanism 210 is configured to bend the path of the e-beam (e.g., using magnetic steering coils) such that the e-beam impinges on the target 206 along a desired scan path (e.g., from one end of the target to the other). The steering mechanism 210 may also implement focusing components to focus the electrons into a generally desirable shape having a suitable focal point. In some embodiments, the steering mechanism 210 may comprise a plurality of individual steering elements (e.g., steering coils) that operate together (e.g., in a sequential fashion) to steer an e-beam along a desired scan path on a target 206. An example of such an embodiment is described below in connection with FIG. 7. The electron accelerator 208 and the steering mechanism 210 (including one or more steering elements) is collectively referred to herein as the "e-beam generator" 202.

In some embodiments, the vacuum chamber 204 may be maintained at pressure of less than $10^{-3}$ Torr. For this and other reasons, the vacuum chamber 204 is generally a relatively expensive and bulky component. The larger the vacuum chamber 204 the more expensive and bulky the x-ray scanning system 200 becomes. As discussed below, various techniques may be employed to keep the size of the vacuum chamber 204 to a minimum and thereby reduce the cost of the resulting apparatus.

After the e-beam exits the steering mechanism 210 through an exit port 212 (described below), the e-beam propagates in a linear direction through the vacuum chamber 204 until it impinges on the target 206. The target 206 may be made of any of a number of suitable materials, and the invention is not limited to the use of any particular type of material. In some embodiments, the target 206 may comprise a metallic material and/or the material used may have an effective atomic number greater than 25. In some embodiments, for example, tungsten molybdenum, or gold, or some combination or alloy thereof, may be the target material of choice. In some embodiments, the target 206 may extend along a substantial distance, e.g., greater than ten centimeters, or greater than fifteen centimeters, or greater than twenty centimeters, or greater than twenty-five centimeters, or greater than thirty centimeters, or greater than thirty-five centimeters, or greater than forty centimeters, or greater than forty-five centimeters, or greater than fifty centimeters, or more.

Figure 3B:
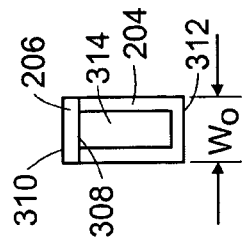
FIGS. 3A-C show various views of an example of an e-beam scanning apparatus that embodies certain inventive concepts disclosed herein.
Figure 3A:
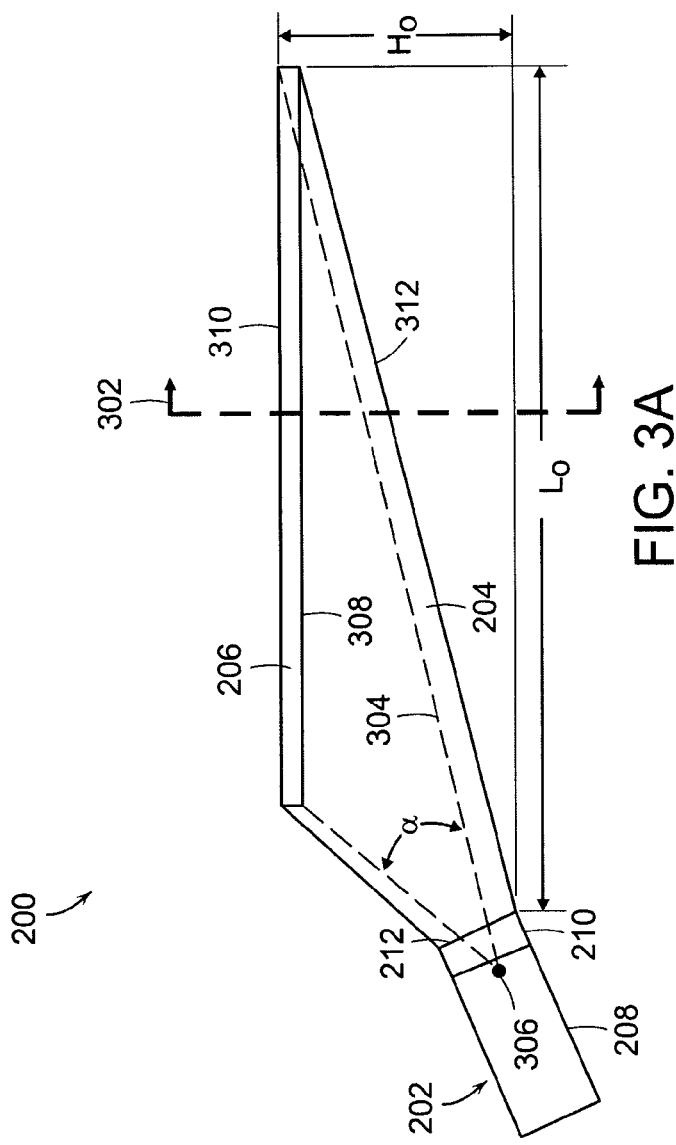
Figure 3C:
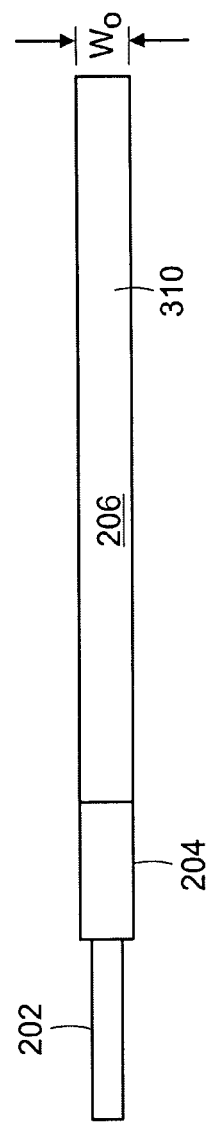

FIGS. 3A-C show, respectively, a side view, a cross-sectional view (taken through section line 302 of FIG. 3A), and a top view of an example of an e-beam scanning apparatus 200 comprising the components described above in connection with FIG. 2. As shown, the apparatus 200 comprises an e-beam generator 202 configured and arranged to sweep an e-beam 304 though a sweep angle α within a vacuum chamber 204. In particular, the e-beam 304 may be swept along a surface 308 of a target 206 so as to cause X-rays to be emanated from the target 206. In the example shown, only a single e-beam generator 202 is employed and the target 206 is substantially linear in shape. It should be appreciated, however, that any number of e-beam generators 202 and a target 206 of virtually any other shape could alternatively be employed, and the invention is not limited to the particular configuration and arrangement shown.

As shown, each e-beam generator 202 may comprise an electron accelerator 208 to create the accelerated e-beam 304, and a steering mechanism 210 to steer the accelerated e-beam 304 through the sweep angle α. The "exit port" 212 of the e-beam generator 202 corresponds to the surface of the region at which the accelerated e-beam 304 is substantially no longer under the effects of the steering mechanism 210 (e.g., one or more steering coils) such that its trajectory is essentially linear and has no significant curvature. An "e-beam origination point" 306 of the e-beam generator 202 is the point at which the accelerated e-beam first begins to be influenced significantly by the steering mechanism 210 and thus begins to be bent by it. In embodiments in which the steering mechanism 210 comprises multiple steering elements that operate together (e.g., in a sequential fashion) to steer an e-beam along a scan path on a target 206, each individual steering element would have a corresponding e-beam origination point as well as a corresponding exit port. The e-beam origination point of an individual steering element in such an embodiment would be the point at which the accelerated e-beam first begins to be influenced significantly by the particular steering element. The exit port of such an individual steering element in such an embodiment would correspond to the surface of the region at which the accelerated e-beam is substantially no longer under the effects of the particular steering element.

In some embodiments, the target 206 may be thin enough that the incident e-beam on a lower surface 308 of the target 206 causes X-rays to be emanated from an upper surface 310 thereof. Such emanated X-rays may then be shaped by a collimator (not shown) for use, for example, in a computed tomography or other x-ray inspection system. In other embodiments, a thicker piece of target material may be used or the target material may be entirely contained within the vacuum chamber 204, and one or more window-covered slits or other apertures (not shown) may be provided in a lower portion 312 or some other portion of the vacuum chamber 204 to allow X-rays to be emitted therethrough. In such embodiments, the vacuum chamber 204 may thus perform the additional function of collimating the generated X-rays to at least some degree.

In the example shown in FIGS. 3A-C, the vacuum chamber 204 occupies at least a portion of a cubic region having a length $L_0$, a height $H_0$, and a width $W_0$. In some embodiments, as in the illustrated example, the total volume occupied by the vacuum chamber 204 may be minimized by sizing it so as to create an internal cavity 314 (see FIG. 3B) that is only slightly larger than the region through which the e-beam 304 sweeps. By way of example, the length $L_0$ may be one hundred centimeters, the height $H_0$ may be ten centimeters, the width $W_0$ may be five centimeters, the target 206 may be ninety centimeters long, and the sweep angle $\alpha$ may be 38.6 degrees. Other embodiments may, of course, employ other dimensions and configurations. The vacuum chamber 204 may, for example, alternatively be made significantly larger than the required sweep region. The vacuum chamber 204 may, for instance, form a rectangular cube having the length $L_0$, the height $H_0$, and the width $W_0$, rather than the more complex design shown.

Figure 4A:
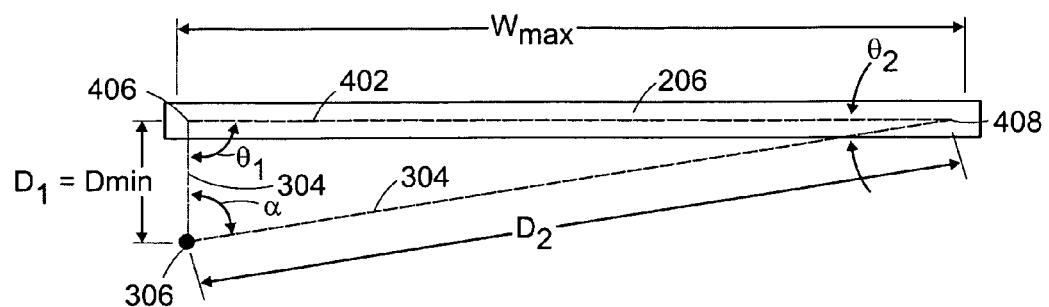
FIGS. 4A-B illustrate schematically how certain components may be configured and arranged in connection with various embodiments.
Figure 4B:
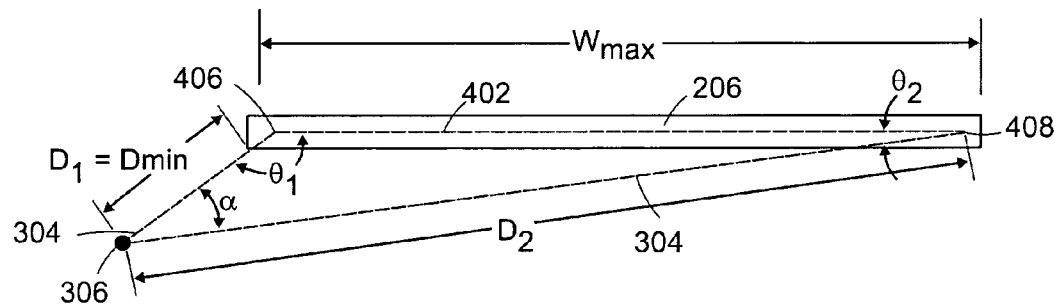
Figure 5A:
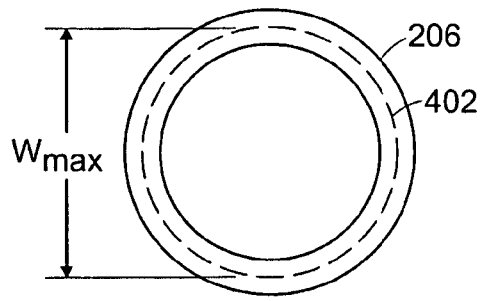
FIGS. 5A-D show a handful of examples of differently shaped targets and correspondingly shaped scan paths that may be employed in various embodiments.
Figure 5B:
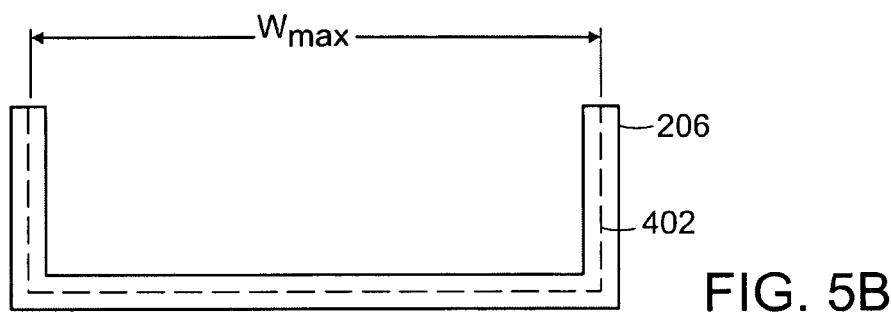
Figure 5C:
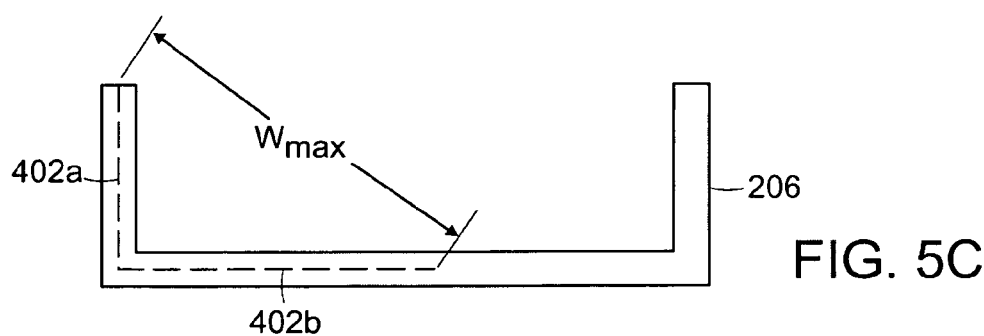
Figure 5D:
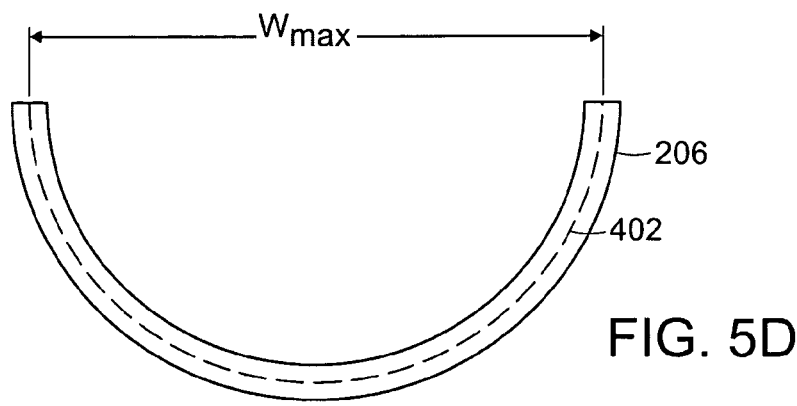

FIGS. 4A-B illustrate schematically how different configurations may be employed in connection with various embodiments of the invention. In the examples shown, dashed line 402 represents a path on a target 206 along which an e-beam from a particular e-beam generator is scanned so as to generate X-rays. As shown in these examples, the target 206 may be substantially linear in shape, as may be the corresponding scan path 402. It should be appreciated, however, that any of a number of differently shaped targets may alternatively be employed, and one or more e-beam scan paths 402 may be controlled so that they correspond to the shape of the particular target that is chosen. Examples of a handful of such differently shaped targets 206, and correspondingly shaped scan paths 402 are illustrated in FIGS. 5A-D. It should further be appreciated that the shape chosen for the target 402 need not occupy a single plane, and may occupy significant portions of three dimensions, if desired. For instance, a helical target such as that disclosed in U.S. Pat. No. 6,735,271, which is incorporated herein by reference in its entirety, and corresponding helical scan path may be employed in certain embodiments.

In some embodiments, the e-beam scan path 402 may follow a linear or a curvilinear path along the length of a target 206. Such a scan path 402 may thus extend a substantial distance along the target 206, e.g., greater than ten centimeters, or greater than fifteen centimeters, or greater than twenty centimeters, or greater than twenty-five centimeters, or greater than thirty centimeters, or greater than thirty-five centimeters, or greater than forty centimeters, or greater than forty-five centimeters, or greater than fifty centimeters, or more.

As shown in FIGS. 5A-D, regardless of the shape of the particular target employed, a maximum dimension between portions of the scan path 402 on the target 206 (identified as $W_{max}$ in the illustrated examples) may be identified. As discussed below, the dimension $W_{max}$ can be useful in defining a relationship between a position of an e-beam generator 202 and a target 206. Alternatively, as also discussed below, the relationship between an e-beam generator 202 and a target 206 may be defined in terms of a total distance an e-beam generated by a particular e-beam generator travels along a surface of a target during a given e-beam scan cycle. Such a distance is referred to herein as the "total e-beam scan distance" or "$D_{total}$." In the example of FIG. 5A (in which the target 206 is circular), for instance, the total e-beam scan distance ($D_{total}$) would be equal to $W_{max} \times \pi$. Similarly, in the example of FIG. 5C, the total e-beam scan distance ($D_{total}$) for the scan path 402 would be equal to the sum of the lengths of its two legs 402a-b. The example of FIG. 5C may, for example, correspond to an embodiment that employs two or more e-beam generators 202 that together are responsible for scanning the entirety of a target, so that each scan path 402 scanned by a particular e-beam generator 202 extends along only a respective portion of the target 206.

Several example configurations of inventive e-beam scanning apparatuses will now be described in connection with FIGS. 4A-B, in which, due to the substantially linear configuration of the target 206 in those examples, the total e-beam scan distance ($D_{total}$) is the same as the maximum dimension ($W_{max}$) between portions of the scan path of a given e-beam generator 202. It should be appreciated, however, that the principles described below in connection with FIGS. 4A-B may apply equally to embodiments such as those shown in FIGS. 5A-D in which those two values are not equal to one another. It should further be appreciated that each target, regardless of the chosen shape, may be configured and arranged so that a maximum number of X-rays are emitted from it in a desired direction for use in inspection of baggage or cargo, medical imaging, or otherwise, and thus may have surfaces that are flat, angled, curved, or otherwise appropriately shaped for the application at hand.

Referring to FIGS. 4A-B (with the understanding that the following description can also apply to embodiments in which the values of $W_{max}$ and $D_{total}$ are different than one another), it can be seen that in some embodiments the minimum distance ($D_{min}$) between the e-beam origination point 306 and the scan path 402 may be substantially smaller than the maximum dimension ($W_{max}$) between portions of the scan path 402, or substantially smaller than the total e-beam scan distance ($D_{total}$) along the path 402, or even substantially smaller than both such values. In some embodiments, for instance, the ratio of $D_{min}$ to one or both of $W_{max}$ and $D_{total}$ may be less than one-to-two. In various other embodiments, the value $D_{min}$ may be, for example, less than forty-five percent, or less than forty percent, or less than thirty-five percent, or less than thirty percent, or less than twenty-five percent, or less than twenty percent, or less than fifteen percent, or less than ten percent, or perhaps less than five percent of the value of one or both of $W_{max}$ and $D_{total}$. By placing the e-beam origination point 306 so as to achieve such a relationship between $D_{min}$ and one or both of $W_{max}$ and $D_{total}$, certain benefits can be achieved such as minimizing the size of the vacuum chamber. It should be appreciated that, in some embodiments, the parameter $D_{min}$ may instead be measured between the exit port 212 (see FIG. 3A) and the scan path, and the above relationships between $D_{min}$ and one or both of $W_{max}$ and $D_{total}$ may likewise exist when $D_{min}$ is so measured.

In some embodiments, such as that described in connection with FIGS. 3A-C, the e-beam generator 202 may be positioned such that the accelerated e-beam 304 intercepts at least some portion of the target 206 at a relatively small acute angle. Such a relationship is illustrated, for example, by the angle $\theta_2$ in the examples of FIGS. 4A-B, and the complement of the angle $\theta_1$ in the example of FIG. 4B. In various embodiments, one or both of such angles may, for example, be made less than forty-five degrees, or less than forty degrees, or less than thirty-five degrees, or less than thirty degrees, or less than twenty-five degrees, or less than twenty degrees, or less than fifteen degrees, or less than ten degrees, or perhaps less than five degrees.

Figure 6A:
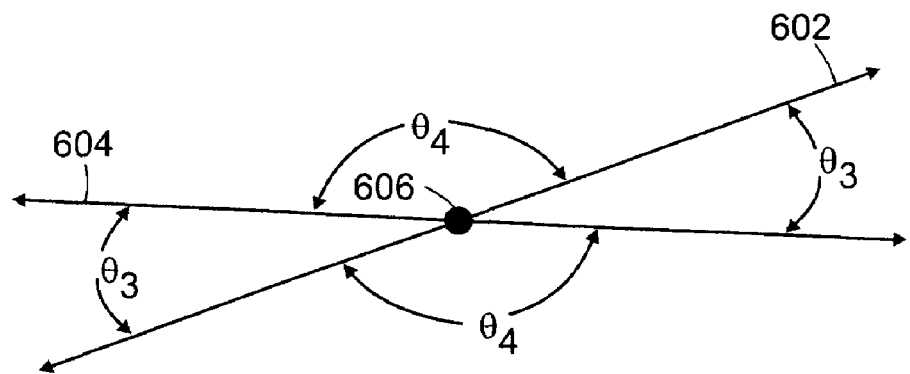
FIG. 6 show pairs of intersecting lines and angles formed therebetween for the purpose of illustrating possible configurations of certain systems disclosed herein.

One way of evaluating the angle of incidence of the accelerated e-beam 304 with the target 206 is by examining the angles formed between (1) lines corresponding to the path of the e-beam 304 when the e-beam 304 impinges upon particular interception points on the target 206 and (2) lines that are tangent to the linear or curvilinear scan path 402 at such interception points. With reference to FIG. 6A, for example, a line 602 may correspond to the path of the e-beam 304 when the e-beam 304 impinges upon a particular interception point on the target 206 and a line 604 may correspond to a line that is tangent to the linear or curvilinear scan path 402 at that same interception point. As can be seen, the lines 602 and 604 intersect at a point 606 and form a first pair of angles $\theta_3$ and a second pair of complementary angles $\theta_4$.

In some embodiments, the e-beam generator 202 may be configured and arranged such that, for at least some interception point along the scan path 402 (and perhaps even for all such interception points), one of the angles $\theta_3$ and $\theta_4$ formed by such lines is less than forty-five degrees, or less than forty degrees, or less than thirty-five degrees, or less than thirty degrees, or less than twenty-five degrees, or less than twenty degrees, or less than fifteen degrees, or less than ten degrees, or perhaps less than five degrees.

In some embodiments, such as those shown in FIGS. 3A-C and FIG. 4B, the position of the e-beam origination point 306 may be beyond an extreme end 406 of the scan path 402 so that lines corresponding to the path of the e-beam at various interception points along the entire length of the scan path always form an acute angle, and are never oriented orthogonally, with respect to lines tangent to the scan path 402 at such interception points.

Figure 6B:
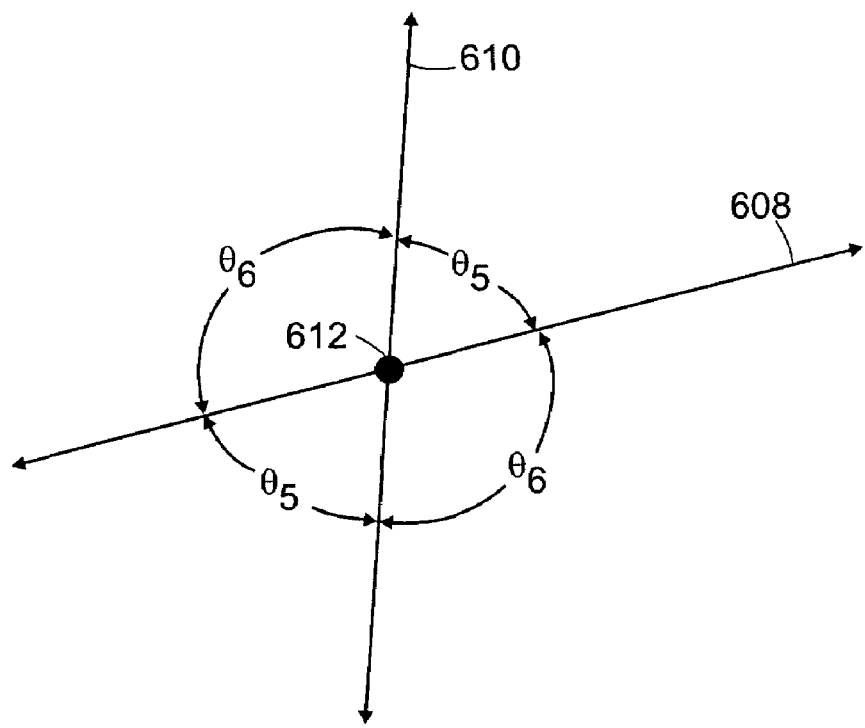

The angle of incidence of the accelerated e-beam 304 with the target 206 may alternatively be evaluated in terms of the angles formed between (1) lines corresponding to the path of the e-beam 304 when the e-beam 304 impinges upon particular interception points on the target 206 and (2) lines that are oriented normal to a surface of the scan path at such interception points. With reference to FIG. 6B, for example, the line 608 may correspond to the path of the e-beam 304 when the e-beam 304 impinges upon a particular interception point on the target 206 and the line 610 may correspond to a line that is oriented normal to a surface of the scan path at that same interception point. As shown, the lines 608 and 610 intersect at a point 612 and form a first pair of angles $\theta_5$ and a second pair of complementary angles $\theta_6$. In various embodiments, the e-beam generator 202 may, for example, be positioned so that, for at least some interception point on the scan path 402 (and perhaps even for all such interception points), the angles $\theta_5$ and $\theta_6$ formed by such lines are both greater than forty-five degrees, or greater than fifty degrees, or greater than fifty-five degrees, or greater than sixty degrees, or greater than sixty-five degrees, or greater than seventy degrees, or greater than seventy five degrees, or greater than eighty degrees, or perhaps greater than eighty five degrees.

It should be appreciated that as the e-beam generator 202 is positioned asymmetrically with the target 206, the e-beam 304 will impinge on the target 206 at increasingly oblique angles, effecting the eccentricity of the focal spot. To compensate for changes in the focal spot of the e-beam 304, the steering mechanism 210 may include focusing means to reshape the e-beam 304 to compensate for the oblique angles at which the e-beam 304 impinges on the target 206.

In some embodiments, for at least one steering element that is configured and arranged to steer an accelerated e-beam 304 along a particular section of the target 206 (such as the steering mechanism 210 in the example of FIGS. 3A-C—an example employing multiple individual steering elements 210a-h is described below in connection with FIG. 7), the steering element may be configured and arranged so that a line corresponding to a path of the accelerated e-beam 306 just before it is influenced significantly by the steering element (i.e., the e-beam origination point 306 of that steering element) forms relatively small angles with respect to lines that are tangent to the linear or curvilinear scan path 402 at the various interception points on the particular portion of the target 206 along which the particular steering element steers the accelerated e-beam 304. With reference to FIG. 6A, for example, the line 602 may correspond to the path of the accelerated e-beam 306 at the e-beam origination point 306 of a steering element and the line 604 may correspond to a line that is tangent to the scan path 402 at a particular interception point on the portion of the target 206 along which the particular steering element steers the accelerated e-beam 304. In some embodiments, the e-beam generator 202 may be configured and arranged such that, for at least some interception point along the particular portion of the target 206 along which the particular steering element steers the accelerated e-beam 304 (and perhaps even for all such interception points), one of the angles $\theta_3$ and $\theta_4$ formed by such lines is less than forty-five degrees, or less than forty degrees, or less than thirty-five degrees, or less than thirty degrees, or less than twenty-five degrees, or less than twenty degrees, or less than fifteen degrees, or less than ten degrees, or less than five degrees, or perhaps even zero degrees.

The orientation of an accelerated e-beam 304 at an e-beam origination point 306 of a particular steering element with respect to the orientation of the particular portion of the target 206 along which the particular steering element steers the accelerated e-beam 304 may alternatively be evaluated in terms of the angles formed between (1) a line corresponding to the path of the accelerated e-beam 304 at the e-beam origination point 306 of the particular steering element and (2) lines that are oriented normal to a surface of the scan path 402 on the particular portion of the target 206 along which the particular steering element steers the accelerated e-beam 304. With reference to FIG. 6B, for example, the line 608 may correspond to the path of the accelerated e-beam 304 at the e-beam origination point 306 of a steering element and the line 610 may correspond to a line that is oriented normal to a surface of the target 206 at a particular interception point along the scan path 402. In various embodiments, the e-beam generator 202 may, for example, be positioned so that, for at least some interception point along the particular portion of the target 206 along which the particular steering element steers the accelerated e-beam 304 (and perhaps even for all such interception points), the angles $\theta_5$ and $\theta_6$ formed by such lines are both greater than forty-five degrees, or greater than fifty degrees, or greater than fifty-five degrees, or greater than sixty degrees, or greater than sixty-five degrees, or greater than seventy degrees, or greater than seventy five degrees, or greater than eighty degrees, or greater than eighty five degrees, or are perhaps equal to ninety degrees.

Referring back to FIGS. 3A-C, it can be seen that the vacuum chamber 204 in the illustrated embodiment is considerably longer in the direction in which the target 206 primarily extends (i.e., the dimension $L_0$) than in the direction perpendicular to the scan path on the target 206 (i.e., the dimension $H_0$). In some embodiments, for each interception point along the scan path on the target 206 (or perhaps just for those interception points along which a particular steering element steers the accelerated e-beam), the maximum dimension of the interior cavity of the vacuum chamber, measured in a plane that contains such interception point and to which a line tangent to the linear or curvilinear scan path at such interception point is normal, may be less than fifty percent, or less than forty-five percent, or less than forty percent, or less than thirty-five percent, or less than thirty percent, or less than twenty-five percent, or less than twenty percent, or less than fifteen percent, or less than ten percent, or perhaps less than five percent, of the total e-beam scan distance along the scan path on the target 206.

As illustrated in FIGS. 4A-B, another way of evaluating certain aspects of the novel systems disclosed herein is by identifying the relationship between (1) the distance $D_1$ between the e-beam origination point 306 and a first extreme end 406 of the scan path 402 (or alternatively between the exit port 212 and the first extreme end 406 of the scan path 402), and (2) the distance $D_2$ between the e-beam origination point 306 and a second extreme end 408 of the scan path 402 (or alternatively between the exit port 212 and the second extreme end 408 of the scan path 402). It should be appreciated that in embodiments in which respective ones of multiple steering elements steer an accelerated e-beam along different portions of a scan path (such as described below in connection with FIG. 7), for a particular steering element, the distance $D_1$ may correspond to a minimal distance between the e-beam origination point of the steering element and the particular portion of the scan path on the surface of the target along which the steering element steers the accelerated e-beam, and the distance $D_2$ may correspond to a maximal distance between the e-beam origination point of the steering element and the particular portion of the scan path on the surface of the target along which the steering element steers the accelerated e-beam. Alternatively, the distances $D_1$ and $D_2$ shown in FIGS. 4A-B may correspond to measurements between the e-beam origination point 306 (or, alternatively, the exit port 212) and the points on the e-beam scan path 402 between which the distance $W_{max}$ (discussed above) is measured.

In any case, as can be seen in FIGS. 4A-B, by increasing the ratio between the distances $D_1$ and $D_2$, the sweep angle $\alpha$ of the scan beam 304 may be reduced without altering the minimum distance $D_{min}$. In various embodiments, the distance $D_1$ may be, for example, less than ninety-five percent, or less than ninety percent, or less than eighty-five percent, or less than eighty percent, or less than seventy-five percent, or less than seventy percent, or less than sixty-five percent, or less than sixty percent, or less than fifty-five percent, or less than fifty percent, or less than forty-five percent, or less than forty percent, or less than thirty-five percent, or less than thirty percent, or less than twenty-five percent, or less than twenty percent, or less than fifteen percent, or less than ten percent, or perhaps less than five percent of the distance $D_2$.

In the embodiment shown in FIGS. 3A-C, the sweep angle $\alpha$ may, for example, be approximately thirty-eight degrees, the angle $\theta_1$ may, for example, be approximately one hundred and thirty-five degrees, the angle $\theta_2$ may, for example, be approximately six degrees, the distance $D_1$ (and $D_{min}$) may, for example, be approximately fourteen centimeters, and the distance $D_2$ may, for example, be approximately one hundred and one-half centimeters. Other embodiments may alternatively be configured so that any one, or some, or perhaps even all, of these values fall within any one, or some, or perhaps even all of the ranges discussed above. In this regard, it should be appreciated that none of the ranges or parameters discussed above is necessarily critical to the invention, and that certain aspects of the invention may be met if only a single such parameter or range, or some particular subset of parameters or ranges, is complied with.

Figure 7:
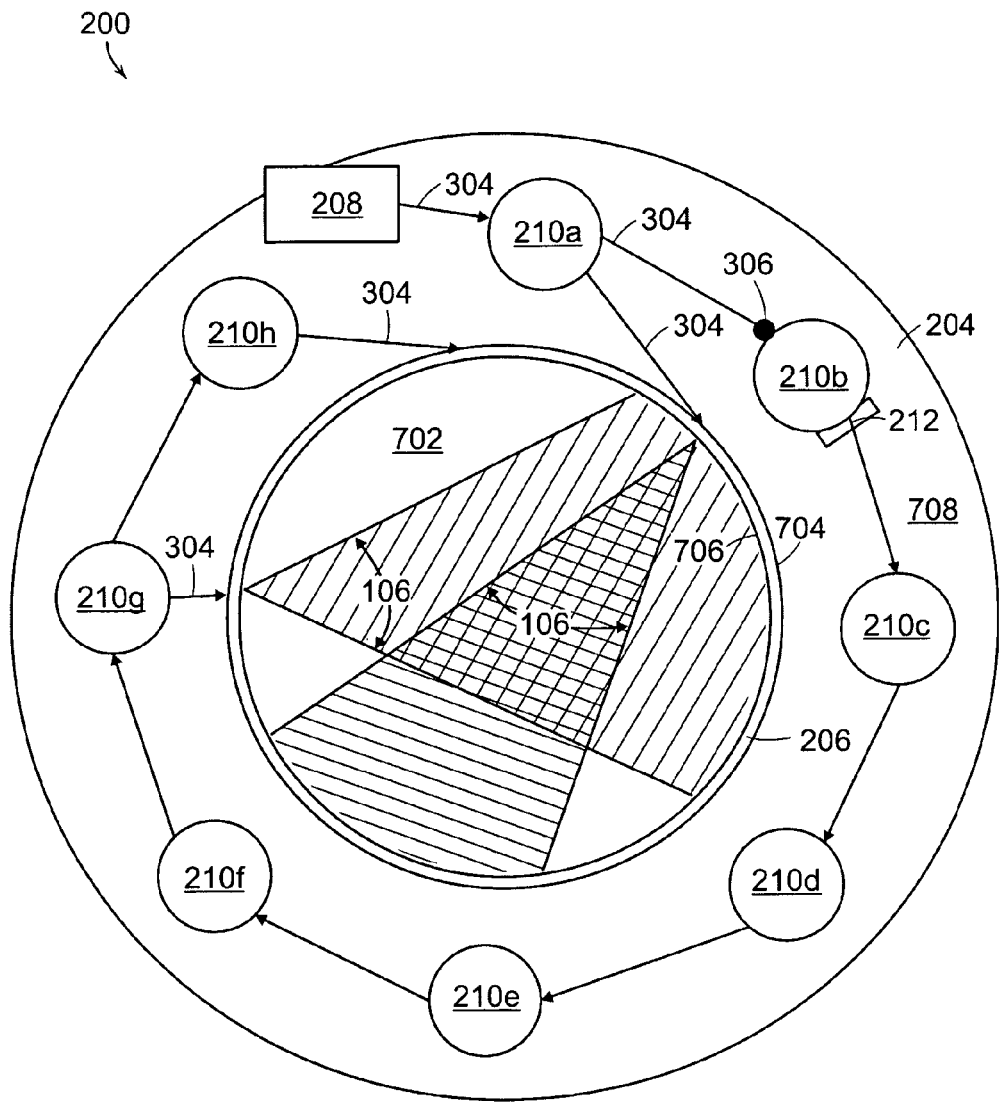
FIG. 7 shows another example of an apparatus that embodies certain inventive aspects disclosed herein.

FIG. 7 shows another example of an apparatus 200 that embodies certain aspects of the inventions disclosed herein. In many ways, the embodiment of FIG. 7 may be viewed as a combination of a group of devices like that shown in FIGS. 3A-C that are arranged in a circle and employ a common vacuum chamber 204. In particular, the illustrated apparatus comprises a vacuum chamber 204 into which an e-beam 304 is introduced by an electron accelerator 208, and a steering mechanism 210 comprising a group of steering elements 210*a-h* configured and arranged to steer the e-beam 304 in a generally circular path. The electron accelerator 208 and the steering elements 210*a-h* can thus be viewed as a common e-beam generator 202. As used herein, "generally circular" is intended to refer to any path forming a substantially closed loop and thus is meant to encompass square paths, triangular paths, and the like. It should be appreciated that a greater or fewer number steering elements 210*a-h* may be employed and such elements may be arranged in any of a number of ways. The invention is not limited to any particular quantity or arrangement of such elements.

As shown, a target 206 may be arranged along some or all of a boundary of the vacuum chamber 204, and one or more of the steering elements 210*a-h* may be controlled so that the e-beam 304 is caused to be scanned along a surface of the target 206 to thereby cause the generation of beams of X-rays 106 within a tunnel 702, e.g., fan beams or cone beams of X-rays within a tunnel of a CT scanner. A suitable collimator (not shown) may, of course, be employed, and one or more groups of detectors (not shown) may be arranged on an opposite side of the tunnel 702 as the one or more scanned sections of the target 206 so as to acquire image data for each of various views of an item under examination. In some embodiments, a suitable conveyor, e.g., a conveyor belt, may be disposed in the tunnel so as to transport items of luggage therethrough to allow the inspection thereof. In other embodiments, a conveyor suitable for transporting a patient through the tunnel, e.g., a slidable patient table, may be disposed in the tunnel to allow the CT scanner to be used for medical imaging applications. (Such conveyor types may also be employed in connection with the other embodiments discussed above to allow such devices to be used for baggage inspection (or other security applications) or for medical imaging (or other imaging applications), as desired).

Similar to the steering mechanism 210 in the embodiment of FIGS. 3A-C, each of the steering elements 210*a-h* in the embodiment of FIG. 7 has an e-beam origination point 306 corresponding to a location at which the steering element first begins to have a significant influence on the trajectory of the e-beam, and also has an exit port 212 corresponding to a surface of the region at which the steering element first ceases to have a significant effect on the e-beam's trajectory. Likewise, each steering element 210*a-h* in the embodiment of FIG. 7 can be associated with a particular scan path 402 on a surface of the target 206 along which it is responsible for sweeping the e-beam 304. In view of these similarities, it should be appreciated that the device of FIG. 7 either embodies, or may be modified to embody, some or all of the particular relationships described above.

In some embodiments, two or more of the steering elements 210*a-h* may be selectively controlled one after another to steer the e-beam 304 along a respective section of the target 206 and thereby scan the e-beam 304 continuously along an extended portion of the target's surface. For example, for a target 206 that is semicircular in shape and surrounds approximately one half of the tunnel 702, the group of steering elements on the same side of the tunnel 204 as the target 206 may be selectively controlled so as to cause the e-beam 304 to be repeatedly scanned along an entire length of the surface of the target 206. In such an embodiment, beams of X-rays 106 may be generated from positions on the target 206 that extend through one hundred and eighty degrees, thereby allowing detectors (not shown) on an opposite side of the tunnel 702 to accumulate image data for a selected number of views throughout that one hundred and eighty degree range. Such an embodiment may thus perform a full CT reconstruction of a scanned cross-section of an item within the tunnel 702. Alternatively, the target 206 may form a full circle and the steering elements 210*a-h* may be selectively controlled to as to cause the e-beam 304 to repeatedly sweep around the entire circumference of the target 206 and thereby generate X-rays through a full three hundred and sixty degree range. The target 206 and associated detectors could be arranged appropriately to allow views throughout the entire 360 degree range to be accumulated. Suitable techniques for arranging the source and detectors to allow image acquisition in either circumstance are disclosed in U.S. Pat. No. 6,725,271, incorporated by reference above.

The target 206 may be placed in any of a number of positions with respect to the steering elements 210*a-h*, and the invention is not limited to any particular orientation of the target 206. The optional position of the target 206 and corresponding configuration of the steering elements 210*a-h* may be selected depending on the application at hand. In some embodiments, the target 206 may be disposed in the same plane as the generally circular path of the e-beam 304, thereby requiring the steering elements 210*a-h* to be capable of steering the e-beam 304 only within a single plane. In other embodiments, more complex steering elements 210*a-h* capable of steering e-beams in multiple planes may alternatively be employed, thus allowing the target 206 to be disposed in a plane above or below that of the steering elements 210*a-h*.

As in the other embodiments describe above, the target 206 may be thin enough that the incident e-beam on a surface 704 of the target 206 exposed to a cavity 708 within the vacuum chamber 204 causes X-rays to be emanated from the opposite surface 706 to a location outside the cavity 708 (i.e., into the tunnel 702). Alternatively, a thicker piece of target material may be used or the target material may be entirely contained within the vacuum chamber 204, and one or more window-covered slits or other apertures (not shown) may be provided about at least a portion of the inner circumference of the vacuum chamber 204 or some other portion of the vacuum chamber 204 to allow X-rays to be emitted therethrough. As with the previous examples, in such embodiments, the vacuum chamber 204 may thus perform the additional function of collimating the generated X-rays to at least some degree. It should be additionally appreciated that, to the extent not already explained, any or all of the other features or functionality of the embodiments or components described above in connection with FIGS. 2-6 may likewise be incorporated into the embodiment of FIG. 7, and vice versa.

Various aspects of the inventions disclosed herein may be used alone, in combination, or in a variety of arrangements not specifically discussed in the embodiments described in the foregoing and is therefore not limited in its application to the details and arrangement of components set forth in the foregoing description or illustrated in the drawings. In particular, the various inventive aspects are not limited for use with any particular type of X-ray scanning device. The disclosed inventive aspects may be used alone or in any combination and are not limited to the combinations illustrated in the embodiments described herein.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

Having described several embodiments in detail, various modifications and improvements will readily occur to those skilled in the art. Such modifications and improvements are intended to be within the spirit and scope of the invention. Accordingly, the foregoing description is by way of example only, and is not intended as limiting. The invention is limited only as defined by the following claims and the equivalents thereto.

What is claimed is:

1. An apparatus for generating X-rays, comprising:
   a vacuum chamber forming an interior cavity that is maintained at a low pressure;
   a target having a surface exposed to the interior cavity of the vacuum chamber;
   an electron accelerator configured and arranged to generate an accelerated electron beam having an energy sufficient to generate X-rays capable of penetrating objects of interest for inspection purposes when the accelerated electron beam impinges upon the surface of the target; and
   a steering element having an electron beam origination point and an exit port, the steering element being configured and arranged to steer an accelerated electron beam through the interior cavity of the vacuum chamber and along at least a particular portion of a linear or curvilinear scan path on the surface of the target so as to cause X-rays capable of penetrating objects of interest for inspection purposes to emanate into an inspection region located outside the interior cavity of the vacuum chamber; and wherein the apparatus is configured and arranged so that each interception point on the particular portion of the scan path on the surface of the target along which the steering element steers the accelerated electron beam, an angle between a line corresponding to a direction in which the accelerated electron beam is traveling at the interception point and a line that is tangent to the scan path at such interception point is less than forty five degrees.

2. The apparatus of claim 1, wherein the apparatus is configured and arranged such that, for at least one interception point on the particular portion of the scan path on the surface of the target along which the steering element steers the accelerated electron beam, an angle between a line corresponding to a direction in which the accelerated electron beam is traveling at the electron beam origination point of the steering element and a line that is tangent to the scan path at such interception point is less than forty five degrees.

3. The apparatus of claim 1, wherein the apparatus is configured and arranged such that a minimal distance between the electron beam origination point of the steering element and the particular portion of the scan path on the surface of the target along which the steering element steers the accelerated electron beam is less than fifty percent of a maximal distance between the electron beam origination point of the steering element and the particular portion of the scan path on the surface of the target along which the steering element steers the accelerated electron beam.

4. The apparatus of claim 1, wherein the apparatus is configured and arranged such that, for each interception point on the particular portion of the scan path on the surface of the target along which the steering element steers the accelerated electron beam, a maximum dimension of the interior cavity of the vacuum chamber, measured in a plane that contains such interception point and to which a line that is tangent to the scan path at such interception point is normal, is less than fifty percent of a total electron beam scan distance along the particular portion of the scan path on the surface of the target along which the steering element steers the accelerated electron beam.

5. The apparatus of claim 1, wherein the apparatus is configured and arranged such that, for each interception point on the scan path on the surface of the target, a maximum dimension of the interior cavity of the vacuum chamber, measured in a plane that contains such interception point and to which a line that is tangent to the scan path at such interception point is normal, is less than fifty percent of a total electron beam scan distance along the scan path on the surface of the target.

6. The apparatus of claim 1, wherein the apparatus is further configured and arranged such that a minimum distance between the exit port of the steering element and the scan path is less than fifty percent of a maximum dimension between portions of the scan path on the target.

7. The apparatus of claim 1, wherein the apparatus is further configured and arranged such that a minimum distance between the exit port of the steering element and the scan path is less than fifty percent of a total electron beam scan distance for the scan path on the target.

8. The apparatus of claim 1, wherein the apparatus is configured and arranged such that the electron beam origination point of the steering element is beyond an extreme end of the scan path.

9. The apparatus of claim 1, wherein:
the particular portion comprises a first linear portion; and
the system further comprises at least one additional steering element configured and arranged to steer the accelerated electron beam through the interior cavity of the vacuum chamber and along a second linear portion of the scan path on the surface of target so as to cause X-rays capable of penetrating objects of interest for inspection purposes to emanate into an inspection region located outside the interior cavity of the vacuum chamber.

10. The apparatus of claim 1, wherein the electron accelerator is configured and arranged to generate the accelerated electron beam so as to have an energy of at least 40 KeV.

11. The apparatus of claim 1, wherein:
the vacuum chamber at least partially surrounds a tunnel; and
the apparatus further comprises a collimator configured and arranged to shape the X-rays generated when the electron beam impinges upon the scan path on the target into a moving beam that passes through the tunnel.

12. The apparatus of claim 11, further comprising a plurality of X-ray detectors arranged in the tunnel diametrically opposed to the scan path on the target.

13. The apparatus of claim 1, wherein the target is configured and arranged such that the scanning of the accelerated electron beam on the surface of the target that is exposed to the interior cavity of the vacuum chamber causes X-rays to be emanated from an opposite surface of the target that is exposed to the inspection region.

14. The apparatus of claim 1, wherein the vacuum chamber comprises a window configured and arranged to allow X-rays emitted from the surface of the target along which the electron beam is scanned to exit the interior cavity of the vacuum chamber and enter the inspection region.

15. The apparatus of claim 1, wherein a total electron beam scan distance along the particular portion of the scan path on the surface of the target along which the steering element steers the accelerated electron beam is more than ten centimeters.

16. An apparatus for generating X-rays into an inspection region, comprising:
a vacuum chamber forming an interior cavity that is maintained at a low pressure;
a target having a first surface exposed to the interior cavity of the vacuum chamber and a second opposing surface, facing the inspection region;
an electron accelerator configured and arranged to generate an accelerated electron beam having an energy sufficient to generate X-rays capable of penetrating objects of interest for inspection purposes when the accelerated electron beam impinges upon the surface of the target;
a first steering element and a second steering element,
the first steering element being configured and arranged to steer the accelerated electron beam through the interior cavity of the vacuum chamber towards the second steering element and along a first portion of the first surface of the target so as to cause X-rays capable of penetrating objects of interest for inspection purposes to emanate from the second surface of the target and into the inspection region located outside the interior cavity of the vacuum chamber, the first steering element being positioned such that an angle between a line corresponding to a direction in which the accelerated electron beam is traveling at an electron beam origination point of the first steering element and a line oriented normal to the first surface of the target at each point along the first portion is greater than forty five degrees; and
the second steering element being configured and arranged to steer the accelerated electron beam through the interior cavity of the vacuum chamber and along a second portion of the first surface of the target, which is at least partially non-overlapping with the first portion of the first surface of the target, so as to cause X-rays capable of penetrating objects of interest for inspection purposes to emanate from the second surface of the target and into the inspection region, the second steering element being positioned such that an angle between a line corresponding to a direction in which the accelerated electron beam is traveling at an electron beam origination point of the second steering element and a line oriented normal to the first surface of the target at each point along the second portion is greater than forty five degrees.

17. The apparatus of claim 16, wherein:
the target is disposed about at least a portion of a tunnel; and
the first and second steering elements steer the accelerated electron beam along the first and second portions of the first surface of the target so as to cause a moving X-ray beam to be generated within the tunnel.

18. The apparatus of claim 16, wherein the apparatus is configured and arranged such that:
for each interception point on a first scan path along the first portion of the first surface of the target along which the first steering element steers the accelerated electron beam, a maximum dimension of the interior cavity of the vacuum chamber, measured in a plane that contains such interception point and to which a line that is tangent to the scan path at such interception point is normal, is less than fifty percent of a total electron beam scan distance along the first scan path; and for each interception point on a second scan path along the second portion of the first surface of the target along which the second steering element steers the accelerated electron beam, a maximum dimension of the interior cavity of the vacuum chamber, measured in a plane that contains such interception point and to which a line that is tangent to the scan path at such interception point is normal, is less than fifty percent of a total electron beam scan distance along the second scan path.

19. A method for generating X-rays, comprising:

generating an accelerated electron beam within a vacuum chamber forming an interior cavity that is maintained at a low pressure and including a target having a surface exposed to the interior cavity of the vacuum chamber, the accelerated electron beam being generated with an energy sufficient to generate X-rays capable of penetrating objects of interest for inspection purposes when the accelerated electron beam impinges upon the surface of the target; and steering the accelerated electron beam with a steering element having an electron beam origination point and an exit port, the steering comprising steering the accelerated electron beam through the interior cavity of the vacuum chamber and along at least a particular portion of a linear or curvilinear scan path on the surface of the target so as to cause X-rays capable of penetrating objects of interest for inspection purposes to emanate into an inspection region located outside the interior cavity of the vacuum chamber, and wherein the apparatus is configured and arranged so that a minimal distance between the electron beam origination point of the steering element and the particular portion of the scan path on the surface of the target along which the steering element steers the accelerated electron beam is less than fifty percent of a maximal distance between the electron beam origination point of the steering element and the particular portion of the scan path on the surface of the target along which the steering element steers the accelerated electron beam.

20. The method of claim 19, further comprising steps of:

collimating the X-rays that are generated when the accelerated electron beam impinges upon the scan path into a moving beam that passes through a tunnel; and acquiring views for a CT scan using a plurality of X-ray detectors arranged in the tunnel diametrically opposed to the first and second portions of the surface of the target.

21. The method of claim 19, wherein:

the steering further comprises, for each interception point on the particular portion of the scan path on the surface of the target along which the steering element steers the accelerated electron beam, steering the accelerated electron beam with an angle of less than forty five degrees between a line corresponding to a direction in which the accelerated electron beam is traveling at the interception point and a line that is tangent to the scan path at such interception point.

22. The method of claim 21, wherein the angle is less than thirty degrees.

23. The method of claim 22, wherein the angle is less than twenty degrees.

24. Apparatus for generating x-ray, comprising:

a vacuum chamber;

a target having a surface within the vacuum chamber;

an electron accelerator configured an arranged to generate an accelerated electron beam; and a steering element having an electron beam origination point and an exit port, the steering element being configured and arranged to steer an accelerated electron beam through the interior of the vacuum chamber and along a scan path on the surface of the target, wherein:

the scan path has a maximum dimension ($W_{max}$) between points on the scan path; and the electron accelerator and steering element are disposed such that:

the minimum distance between the origination point and any point on the scan path ($D_{min}$) is less than one half the maximum dimension ($W_{max}$); and the electron accelerator is offset relative to the surface of the target whereby the accelerated electron beam impinges on the surface at an oblique angle at each point along the scan path.

25. The apparatus of claim 24, wherein the steering element comprises a focusing mechanism to reshape the beam to compensate for eccentricity of a focal spot of the beam associated with the oblique angle at each point along the scan path.

26. The apparatus of claim 25, wherein the steering element steers the electron beam through a sweep angle within the vacuum chamber of less than 40 degrees.

* * * * *